United States Patent [19]

Noble

[11] Patent Number: 4,574,152

[45] Date of Patent: Mar. 4, 1986

[54] CEPHALOSPORIN COMPOUNDS

[75] Inventor: David Noble, Slough, England

[73] Assignee: Glaxo Group Limited, London, England

[21] Appl. No.: 457,940

[22] Filed: Jan. 14, 1983

[30] Foreign Application Priority Data

Jan. 15, 1982 [GB] United Kingdom ................ 8201139

[51] Int. Cl.$^4$ .......................................... C07D 501/02
[52] U.S. Cl. .......................................... 544/4; 544/30; 544/21
[58] Field of Search .................. 544/22, 30, 4, 28, 29, 544/26, 27, 21; 424/246

[56] References Cited

U.S. PATENT DOCUMENTS 3,661,901 5/1972 Bickel et al. ..................... 260/243 C
4,204,058 5/1980 Vértesy et al. .......................... 544/4

*Primary Examiner*—Nicholas S. Rizzo
*Attorney, Agent, or Firm*—Bacon & Thomas

[57] ABSTRACT

Ternary complexes comprising a 7-[D-5-amino-5-carboxypentanamido] cephalosporin complexed with copper (II) ions and an organic nitrogen base as well as a process for their preparation are described. The complexes may be used in the isolation and/or purification of cephalosporin fermentation products.

12 Claims, No Drawings

CEPHALOSPORIN COMPOUNDS

This invention relates to a novel process for the isolation and purification of cephalosporin compounds substituted at the 7β-position by a D-5-amino-5-carboxypentanamido group. The invention also relates to novel compounds obtained in such a process.

The cephalosporin compounds in this specification are named with reference to "cepham" after J. Amer. Chem. Soc. 1962, 94, 3400, the term "cephem" referring to the basic cepham structure with one double bond.

Cephalosporin compounds are widely used as antibiotics in the treatment of diseases caused by pathogenic bacteria in human beings and animals. Such cephalosporins are generally prepared by chemical modification at the 7-position, and sometimes at the 3-position, of cephalosporins prepared by fermentation. All known cephems prepared by fermentation have, as their 7-position substituent, a D-5-amino-5-carboxypentanamido group.

Thus, for example, starting materials in processes for the preparation of pharmacologically useful cephalosporin compounds include cephalosporin C, i.e. (6R,7R)-7-[D-5-amino-5-carboxypentanamido]-3-(acetoxymethyl)ceph-3-em-4-carboxylic acid and salts thereof, such as its sodium or potassium salt, as well as desacetyl- and desacetoxycephalosporin C, that is the 3-hydroxymethyl and 3-methyl analogues of cephalosporin C respectively, and their salts.

Other interesting cephalosporin compounds having a 7-[D-5-amino-5-carboxypentanamido] group include, for example, the cephamycins such as cephamycin C.

In the preparation of cephalosporins having a 7-[D-5-amino-5-carboxypentanamido] group, the compounds are often produced in an impure form in aqueous media, for example in a culture broth from a microbiological process for the synthesis of the compounds, in particular a fermentation process. The purification of such impure forms is, however, made difficult by the amphoteric properties of the D-5-amino-5-carboxypentanamido group; thus their purification and isolation has previously been problematical.

British Patent Specification No. 1270448 describes a process for isolating and purifying cephalosporin C via the formation of a 1:1 complex of cephalosporin C with a divalent heavy metal, e.g. copper, nickel, lead, cobalt, iron, manganese, mercury, cadmium or preferably zinc. The 1:1 complex may be prepared by adding a water-soluble salt of the divalent heavy metal to a dilute and/or impure solution of cephalosporin C, which may be in the form of a salt with inter alia an organic base although the base is not incorporated into the complex. However, such 1:1 complexes are formed relatively slowly and are usually precipitated by addition of an organic solvent and/or by chilling.

We have now discovered that 7-[D-5-amino-5-carboxypentanamido] cephalosporins may advantageously be purifed and isolated from aqueous media by precipitation as a ternary complex comprising the cephalosporin complexed with copper (II) ions and an organic nitrogen base.

Thus, in one aspect, the invention provides a process for preparing a ternary complex comprising a 7-[D-5-amino-5-carboxypentanamido] cephalosporin complexed with copper (II) ions and an organic nitrogen base, which process comprises contacting said cephalosporin in an aqueous medium with copper (II) ions and an organic nitrogen base whereby said complex is precipitated.

In general, the complex may be precipitated relatively quickly, for example in 15-105 minutes, without chilling and/or addition of an organic solvent. This is particularly advantageous in the extraction of cephalosporins from crude culture filtrates on a production scale.

The cephalosporin starting material for the process of the invention may be any 7-[D-5-amino-5-carboxypentanamido] cephalosporin such as, for example, the above mentioned cephalosporin C, desacetylcephalosporin C, desacetoxycephalosporin C, cephamycins e.g. cephamycin C, and salts thereof. The process of the invention may be especially useful in the isolation and purification of such a cephalosporin compound from a crude culture filtrate obtained in a microbiological process for its preparation, in particular, a fermentation process. The aqueous medium used in the process may conveniently comprise a crude culture filtrate derived from a fermentation broth.

The ternary complex produced in the process of the invention comprising the starting 7-[D-5-amino-5-carboxypentanamide] cephalosporin compound complexed with copper (II) ions and the organic nitrogen base is novel and forms a further feature of the invention. The complex according to the invention generally contains substantially equimolar amounts of the cephalosporin compound, copper (II) ions and the organic nitrogen base.

In a still further aspect, the invention provides a process for the preparation of a 7-[D-5-amino-5-carboxypentanamido]cephalosporin compound which comprises the steps of (a) precipitating a ternary complex of said cephalosporin compound from an aqueous medium containing said cephalosporin compound, copper (II) ions and an organic nitrogen base; (b) separating said complex from the aqueous medium; and (c) treating said separated complex to yield the desired cephalosporin compound.

The copper (II) ions may be provided in the aqueous medium by dissolving therein a copper (II) compound soluble in said medium or adding thereto a medium containing a copper (II) compound. Examples of such compounds include water-soluble copper (II) salts, such as copper (II) acetate, chloride or sulphate. Alternatively, a sparingly soluble compound such as copper (II) carbonate may be added.

Organic nitrogen bases which may be used according to the invention include, for example, $C_6$–$C_{15}$ aliphatic primary amines such as n-octylamine and dodecylamine, aromatic amines such as aniline and o-toluidine, nitrogen heterocyclic compounds such as quinoline, and aralkyl primary amines having at least two carbon atoms in the alkyl moiety such as 2-phenylethylamine.

In the process of the invention, the cephalosporin, copper (II) ions and organic nitrogen base may be mixed together in any appropriate manner. For example, the organic nitrogen base may be added to an aqueous medium containing the cephalosporin and the copper (II) ions or the copper (II) ions may be added to an aqueous medium containing the cephalosporin and the organic nitrogen base.

In general, it is convenient to add an equimolar amount of copper (II) ions in relation to the amount of cephalosporin which it is wished to precipitate. In some circumstances, however, such as in the case of culture broth filtrates, it may be desirable to add an excess to allow for take-up of copper (II) ions by side reactions and impurities. It is generally advantageous to use an excess of base, e.g. up to a twenty-fold molar excess in relation to the cephalosporin.

In the precipitation of the cephalosporin complex, it has been found that it may be appropriate to maintain the pH of the aqueous medium at between 5 and 8, in order to ensure effective precipitation and to maintain the stability of the cephalosporin. For example, with the more basic amines it has been found that it may be necessary to add acid in order to precipitate the complex.

The precipitated cephalosporin complex may be separated from the aqueous medium from which it is formed according to conventional techniques e.g. by filtration or centrifugation. The thus separated complex may be washed and dried (e.g. under vacuum), as desired.

The purified 7-[D-5-amino-5-carboxypentanamido] cephalosporin may conveniently be recovered from the ternary complex by any appropriate method which removes the copper therefrom. Such a method may thus be conveniently carried out by suspending or dissolving the complex in a suitable medium, usually an aqueous medium, such that after removal of the copper the cephalosporin remains in solution, from which it may be recovered by methods well known in the art. The copper may, for example, be removed as an insoluble salt, such as a sulphide, or complex or may be extracted as a soluble salt or complex. Such methods of removing copper are well known in the art, e.g. as described in Marcus and Kertes, "Ion exchange and solvent extraction of metal complexes", Wiley Interscience 1969.

Thus, for example, the complex may conveniently be suspended in an aqueous medium, if desired after grinding the complex to a suitable particle size for suspension, and then precipitating the copper ions e.g. by addition of hydrogen sulphide, acetyl acetone, or pyridine together with a thiocyanate salt, e.g. potassium thiocyanate. The precipitated copper (II) compound may then be separated off, e.g. by centrifugation or filtration and the purified 7-[D-5-amino-5-carboxypentanamido] cephalosporin compound may be recovered from the supernatant aqueous solution by methods well known in the art.

The complex according to the invention may also be used directly as the starting material for subsequent chemical processing of the 7-[D-5-amino-5-carboxypentanamido] cephalosporin.

The invention will now be illustrated by the following non-limiting Examples.

In each case, the amount of cephalosporin in the complex was determined as follows:- a weighed sample (about 25 mg) of complex was suspended in water (5 ml) and treated with hydrogen sulphide. The precipitated copper (II) sulphide was centrifuged off and the supernatant was diluted to 100 ml with water. A portion (10 ul) of the diluted supernatant was applied to a chromatography column (250 mm length × 5 mm internal diameter) of Spherisorb ODS $C_{18}$ and eluted at about 1.5 ml/min. with a mixture of 0.1M citric acid in water and acetonitrile (87:13 respectively v/v) at 55° C. The eluted cephalosporin was detected by uv spectroscopy at 260 nm, and the peak area was compared with that of a standard.

The amount of quinoline in the complexes prepared according to Examples 16 and 17 was determined as follows:- a weighed sample of complex (about 25 mg) was dissolved in 5% (w/v) aqueous sodium carbonate (5 ml) and the solution extracted with butan-1-ol (4×5 ml). Combined extracts were diluted to 100 ml with butan-1-ol and examined by u.v. spectroscopy. Absorbance at 300 nm was compared with that of a standard solution of quinoline (about 60 ug/ml).

The amount of copper in the complexes prepared according to Examples 16 and 17 was determined as follows:- a weighed sample of complex (about 100 mg) was suspended in water (5 ml) and treated with hydrogen sulphide gas. The precipitated copper (II) sulphide was centrifuged off and the supernatant discarded. The precipitate was resuspended in water (10 ml) then centrifuged off again and the wash discarded. The water wash was repeated once, the precipitate was dried at 110° C. overnight and weighed. The copper content of the complex was estimated from the weight of copper (II) sulphide produced.

EXAMPLE 1

Preparation of an insoluble complex from cephalosporin C, copper (II) acetate and aniline Water (400 ml) containing potassium cephalosporin C (10 g containing 77% cephalosporin C free acid) was mixed with water (100 ml) containing copper (II) acetate monohydrate (5 g). Aniline (9.1 ml) was added dropwise and stirred in vigorously. After 20 min the precipitate which formed was filtered off and washed successively with water (50 ml), methanol (150 ml) and acetone (100 ml). The solid was dried under vacuum and weighed (9.5 g, containing 67% cephalosporin C free acid).

EXAMPLE 2

Preparation of an insoluble complex from cephalosporin C, copper (II) acetate and quinoline The procedure of Example 1 was repeated, except that quinoline (12 ml) was used instead of aniline. The isolated solid was dried under vacuum and weighed (11.0 g, containing 65% cephalosporin C free acid).

EXAMPLE 3

Preparation of an insoluble complex from cephalosporin C, copper (II) sulphate and n-octylamine Water (400 ml) containing potassium cephalosporin C (10 g containing 77% cephalosporin C free acid) was mixed with water (100 ml) containing copper (II) sulphate pentahydrate (6.25 g). n-Octylamine (16.5 ml) was added dropwise and stirred in vigorously. The pH of the reaction mixture was adjusted to 5.5 with acetic acid. After 25 min the precipitate was filtered off, and washed with water (100 ml), methanol (200 ml) and acetone (100 ml). The solid was dried out vacuum and weighed (10.8 g, containing 41% cephalosporin C free acid).

EXAMPLE 4

Preparation of an insoluble complex from cephalosporin C, copper (II) sulphate and 2-phenylethylamine The procedure of Example 3 was repeated, except that 2-phenylethylamine (12.6 ml) was used instead of octylamine, and the pH of the reaction was adjusted to 6.4 with acetic acid. The isolated solid was dried under vacuum and weighed (6.9 g containing 53% cephalosporin C free acid).

EXAMPLE 5

Preparation of an insoluble complex from desacetylcephalosporin C, copper (II) acetate and quinoline Water (100 ml) containing potassium desacetylcephalosporin C (5.75 g containing 72% desacetylcephalosporin C free acid) was mixed with water (50 ml) containing copper (II) acetate monohydrate (2 g) and stirred vigorously. Quinoline (5 ml) was then stirred in and after 20 min. the precipitate which formed was allowed to settle. After a further 20 min. the precipitate was filtered off and washed with water (40 ml), methanol (60 ml) and acetone (40 ml). The solid was dried under vacuum and weighed (5.2 g, containing 62% desacetylcephalosporin C free acid).

| Analysis | % Found | Theoretical %* |
|---|---|---|
| C | 46.04 | 48.97 |
| H | 4.41 | 4.29 |
| N | 9.31 | 9.93 |
| S | 5.53 | 5.68 |
| Cu | 11.31 | 11.27 |

*Calculated for the 1:1:1 complex $C_{23}H_{24}N_4O_7SCu$.

The i.r. spectrum of the complex in a Nujol mull exhibited the following principal absorption bands:- 3280 (NH), 1750 ($\beta$-lactam), 1658 and 1542 (sec. amide), 1630 and 1514 $cm^{-1}$.

EXAMPLE 6

Preparation of an insoluble complex from desacetylcephalosporin C, copper (II) sulphate and quinoline The procedure of Example 5 was repeated, except that copper (II) sulphate pentahydrate (2.5 g) was used instead of the copper (II) acetate. The isolated solid was dried under vacuum and weighed (5.4 g, containing 61% desacetylcephalosporin C free acid).

| Analysis | % Found | Theoretical %* |
|---|---|---|
| C | 46.45 | 48.97 |
| H | 4.48 | 4.29 |
| N | 9.42 | 9.93 |
| S | 5.44 | 5.68 |
| Cu | 10.81 | 11.27 |

*Calculated for the 1:1:1 complex $C_{23}H_{24}N_4O_7SCu$

EXAMPLE 7

Preparation of insoluble complex from desacetylcephalosporin C, copper (II) acetate and n-octylamine Water (400 ml) containing potassium desacetylcephalosporin C (10 g containing 74% free acid) was mixed with water (100 ml) containing copper (II) acetate monohydrate (5 g). n-Octylamine (8.25 ml) was then added dropwise with vigorous stirring. The pH of the reaction mixture was lowered to 6.5 with acetic acid. The precipitate was filtered off after 15 min. and washed with water (100 ml), methanol (150 ml) and acetone (100 ml). The isolated solid was dried under vacuum and weighed (7.7 g, containing 53% desacetylcephalosporin C free acid).

EXAMPLE 8

Preparation of an insoluble complex from desacetylcephalosporin C, copper (II) acetate and aniline The procedure of Example 7 was repeated, except that aniline (9.1 ml) was used instead of n-octylamine and the pH of the reaction mixture was not adjusted. The isolated solid was dried under vacuum and weighed (9.6 g, containing 66% desacetylcephalosporin C free acid).

EXAMPLE 9

Purification of desacetylcephalosporin C

Water (650 ml) containing potassium desacetylcephalosporin C (20 g, containing 74% desacetylcephalosporin C free acid) was mixed with water (200 ml) containing copper (II) sulphate pentahydrate (12.5 g). Quinoline (19 ml) was then added with vigorous stirring. After 30 mins. the precipitate was filtered off and washed with water (260 ml), methanol (390 ml) and acetone (260 ml) and dried under vacuum.

The solid was suspended in water (300 ml) and treated with hydrogen sulphide. The precipitated copper (II) sulphide was filtered off using cellulose (Rettenmaier BEOO) as a filter aid. The filtrate was filtered again through Whatman No. 54 paper. The final filtrate was adjusted to pH 7.7 with potassium hydroxide and extracted with butan-1-ol (500 ml). The aqueous phase was filtered through Whatman No. 54 paper and slowly added to acetone (2500 ml). After 30 min the potassium desacetylcephalosporin C which precipitated was filtered off and washed with acetone. The solid was dried under vacuum and weighed (13.9 g, containing 82% desacetylcephalosporin C free acid).

EXAMPLE 10

Isolation of desacetylcephalosporin C from filtered fermentation broth (a) A fermentation broth containing desacetylcephalosporin C was filtered and diluted with water. A portion (1600 ml) was mixed with copper (II) acetate monohydrate in a 2:1 molar ratio to the cephalosporin. Quinoline was then added with vigorous stirring in a 7:1 molar ratio to the cephalosporin. After 45 min the precipitated complex was filtered off, washed with water (250 ml), methanol (1 liter) and acetone (500 ml) and dried under vacuum. The solid contained 75% of the desacetylcephalosporin C contained in the initial fermentation broth.

(b) A portion of the complex (20.0 g, containing 37% desacetylcephalosporin C free acid) was ground in a mortar and resuspended in water (200 ml). Hydrogen sulphide gas was passed through the suspension for 10 min and the precipitated copper (II) sulphide was centrifuged off. The supernatant was filtered through Whatman No. 54 paper and the filtrate was adjusted to pH 7.7 with 40% (w/v) potassium hydroxide. The resulting emulsion was dripped into acetone (1600 ml) over 20 min and stirred for a further 20 min. The suspension was allowed to stand for 15 h at 4° C. The solid was then filtered off, washed with acetone and dried under vacuum.

The dry solid (9.1 g) contained 66% desacetylcephalosporin C free acid.

EXAMPLE 11

Isolation of desacetylcephalosporin C from filtered fermentation broth (a) A fermentation broth containing desacetylcephalosporin C was filtered and diluted with water. A portion (1600 ml) was mixed with copper (II) acetate monohydrate in a 2:1 molar ratio to the cephalosporin. Quinoline was then added with vigorous stirring in a 7:1 molar ratio to the cephalosporin. After 45 min. the precipitated complex was filtered off, washed with water (250 ml), methanol (1 liter) and acetone (500 ml) and dried under vacuum. The solid contained 75% of the desacetylcephalosporin C contained in the initial fermentation broth.

(b) A portion of the complex (10 g, containing 37% desacetylcephalosporin C free acid) was suspended in water (100 ml). Acetylacetone (7.5 ml) was added, and the mixture was stirred for 60 min. The mixture was then filtered. The filtrate was adjusted to pH 7.5 with 40%(w/v) potassium hydroxide and was dripped slowly into acetone (1050 ml). After standing overnight at room temperature, the solid was filtered off, washed with acetone, and dried under vacuum.

The dry solid (3.3 g) contained 55% desacetylcephalosporin C free acid.

EXAMPLE 12

Isolation of cephalosporin C from filtered fermentation broth (a) A fermentation broth containing cephalosporin C was filtered and diluted with water. A portion (1600 ml) was mixed with copper (II) acetate monohydrate in a 4:1 molar ratio to the cephalosphorin. Quinoline was then added with vigorous stirring in a 13:1 molar ratio to the cephalosphorin. After 45 min. the precipitated complex was filtered off, washed with water (500 ml), methanol (1 liter) and acetone (500 ml), and dried under vacuum. The solid contained 90% of the cephalosporin C contained in the initial fermentation broth.

(b) A portion of the complex (10 g, containing 41% cephalosporin C free acid) was suspended in water (100 ml) and mixed with pyridine (5 ml). Potassium thiocyanate (10 g) was then stirred in and the pH of the mixture was reduced to 6.5 with acetic acid. After 30 min. the suspended solids were centrifuged off (about 1500 g for 30 min.) and the supernatant was dripped into acetone (750 ml) and stirred. After 30 min. the precipitated solid was filtered off, washed with acetone, and dried.

The dry solid (5.7 g) contained 41% cephalosporin C free acid.

(c) A portion of the complex (10 g, containing 41% cephalosporin C free acid) was suspended in water (100 ml). Hydrogen sulphide gas was passed through the suspension for 15 min. Foaming was prevented with a few drops of n-butanol. The precipitated copper sulphide was centrifuged off and the supernatant was filtered. The filtrate was adjusted to pH 7.6 with 40% (w/v) potassium hydroxide and extracted with an equal volume of n-butanol. The aqueous phase was separated off and dripped into acetone (700 ml) over 45 min. The precipitate was filtered off, washed with acetone and dried under vacuum.

The dry solid (4.9 g) contained 53% cephalosporin C free acid.

EXAMPLE 13

Preparation of an insoluble complex from cephalosporin C, copper (II) acetate and aniline A fermentation broth containing cephalosporin C was filtered and diluted with water. A portion was mixed with copper (II) acetate monohydrate (30 g) and aniline (45.5 ml). The mixture was stirred for 105 mins, and then filtered. The precipitated complex was washed with water (250 ml), methanol (750 ml) and acetone (500 ml) and then dried under vacuum. The solid (33.8 g) contained 23% cephalosporin C free acid.

EXAMPLE 14

Preparation of an insoluble complex from desacetoxycephalosporin C, copper (II) acetate and quinoline.

Desacetoxycephalosporin C (101 mg) was dissolved in water (4 ml) and mixed with a 5% (w/v) solution of copper (II) acetate monohydrate (1 ml). Quinoline (130 mg) was then added with vigorous mixing. After 15 min. the precipitated complex was centrifuged off and washed with water (3 ml).

The precipitate was shown to contain desacetoxycephalosporin C by resuspending it in water (25 ml) and treating it with hydrogen sulphide gas. After centrifuging off the precipitate of copper sulphide the supernatant was shown to contain 92% of the original desacetoxycephalosporin C.

EXAMPLE 15

Preparation of an insoluble complex from cephamycin C, copper (II) acetate and quinoline An impure sample of cephamycin C (100 mg) was dissolved in water (4 ml) and mixed with a 5% (w/v) solution of copper (II) acetate monohydrate (1 ml). The pH of the mixture was adjusted to 6.0 with 40% (w/v) potassium hydroxide. Quinoline (120 l) was then added with vigorous mixing. After 15 min. the precipitated complex was centrifuged off and suspended in water (5 ml).

The resuspended precipitate was treated with hydrogen sulphide gas. After centrifuging off the precipitate of copper sulphide the supernatant was shown to contain 32% of the original cephamycin C.

EXAMPLE 16

Preparation of an insoluble complex from desacetylcephalosporin C, copper (II) acetate and quinoline Water (115 ml) containing potassium desacetylcephalosporin C (5.0 g containing 82% desacetylcephalosporin C free acid) was mixed with water (100 ml) containing copper (II) acetate monohydrate (3 g) and stirred vigorously. Quinoline (4.7 ml) was then added and stirring continued for 2 hours. The precipitate which formed was filtered off and washed successively with the following:

(i) Water (2×50 ml).
(ii) Methanol containing 2% (v/v) quinoline (3×50 ml).
(iii) Acetone containing 2% (v/v) quinoline (2×50 ml).
(iv) Acetone (2×50 ml).

The solid was dried under vacuum and weighed (6.35 g). Assay of the solid for desacetylcephalosporin C free acid, quinoline and copper showed these to be present in a molar ratio of approximately 1:1:1.

|  | % Found |
|---|---|
| Desacetylcephalosporin C free acid | 62.4 |
| Quinoline | 23.5 |
| Copper | 13.1 |

EXAMPLE 17

Preparation of an insoluble complex from desacetylcephalosporin C, copper (II) acetate and quinoline.

Precipitation of the complex was carried out as described in Example 16 above. The precipitate was filtered off and washed successively with the following:
(i) Water (2×50 ml).
(ii) Acetone containing 2% (v/v) quinoline (3×50 ml).
(iii) Acetone (3×50 ml).

The solid was dried under vacuum and weighed (6.30 g). Assay of the solid for desacetylcephalosporin C free acid, quinoline and copper showed these to be present in a molar ratio of approximately 1:1:1.

|  | % Found |
|---|---|
| Desacetylcephalosporin C free acid | 63.7 |
| Quinoline | 22.4 |
| Copper | 13.4 |

I claim:

1. A ternary complex comprising a 7-[D-5-amino-5-carboxy-pentanamido]cephalosporin complexed with copper (II) ions and an organic nitrogen base containing from 6 to 15 carbon atoms selected from aliphatic primary amines, aromatic amines, nitrogen heterocyclic compounds and aralkyl primary amines having at least two carbon atoms in the alkyl moiety.

2. A complex according to claim 1 which contains substantially equimolar amounts of the cephalosporin, copper (II) ions and the organic nitrogen base.

3. A complex according to claim 1 wherein the cephalosporin is selected from cephalosporin C, desacetylcephalosporin C, desacetoxycephalosporin C and cephamycin C.

4. A complex according to claim 1 wherein the organic nitrogen base is selected from n-octylamine, dodecylamine, aniline, o-toluidine, quinoline and 2-phenylethylamine.

5. A process for the preparation of the ternary complex according to claim 1 which comprises contacting the 7-[D-5-amino-5-carboxypentanamido]cephalosporin and/or a salt thereof in an aqueous medium with copper (II) ions and an organic nitrogen base whereby said complex is precipitated.

6. A process according to claim 5 wherein the cephalosporin in an aqueous medium comprises a crude culture filtrate derived from a cephalosporin fermentation broth.

7. A process according to claim 5 wherein from 5 to 20 moles of the organic nitrogen base is used per mole of the cephalosporin.

8. A process according to claim 5 wherein the pH of the aqueous medium is maintained in the range of 5 to 8.

9. A process for the isolation of a 7-[D-5-amino-5-carboxypentanamido]cephalosporin compound which comprises the steps of (a) precipitating a ternary complex of said cephalosporin compound from an aqueous medium containing said cephalosporin compound, copper (II) ions and an organic nitrogen base; (b) separating said complex from the aqueous medium; and (c) treating said separated complex to yield the desired cephalosporin compound.

10. A process according to claim 6 wherein from 5 to 20 moles of the organic nitrogen base is used per mole of the cephalosporin.

11. A process according to claim 6 wherein the pH of the aqueous medium is maintained in the range of 5 to 8.

12. A process according to claim 7 wherein the pH of the aqueous medium is maintained in the range of 5 to 8.

* * * * *